(12) United States Patent
Hubbell et al.

(10) Patent No.: US 10,765,774 B2
(45) Date of Patent: Sep. 8, 2020

(54) HEMOSTATIC PAD ASSEMBLY KIT AND METHOD

(71) Applicant: Ethicon, Inc., Someriville, NJ (US)

(72) Inventors: Randolph W. Hubbell, Doylestown, PA (US); James Eckhardt, Skillman, NJ (US); Jerome Riebman, Basking Ridge, NJ (US); Yufu Li, Bridgewater, NJ (US); Michael Elser, New Hope, PA (US)

(73) Assignee: Ethicon, Inc., Somerville, NJ (US)

( * ) Notice: Subject to any disclaimer, the term of this patent is extended or adjusted under 35 U.S.C. 154(b) by 1144 days.

(21) Appl. No.: 13/937,292

(22) Filed: Jul. 9, 2013

(65) Prior Publication Data

US 2015/0017225 A1    Jan. 15, 2015

(51) Int. Cl.
| | |
|---|---|
| *A61L 15/64* | (2006.01) |
| *A61L 15/44* | (2006.01) |
| *A61L 15/28* | (2006.01) |
| *A61L 15/26* | (2006.01) |

(52) U.S. Cl.
CPC ............... *A61L 15/64* (2013.01); *A61L 15/26* (2013.01); *A61L 15/28* (2013.01); *A61L 15/44* (2013.01); *A61L 2300/252* (2013.01); *A61L 2300/254* (2013.01); *A61L 2300/418* (2013.01); *A61L 2400/04* (2013.01)

(58) Field of Classification Search
CPC . A61L 15/64; A61L 2300/418; A61L 2400/04
See application file for complete search history.

(56) References Cited

U.S. PATENT DOCUMENTS

| | | | |
|---|---|---|---|
| 4,002,173 | A | 1/1977 | Manning |
| 4,453,939 | A | 6/1984 | Zimmerman et al. |
| 6,706,690 | B2 | 3/2004 | Reich et al. |
| 6,762,336 | B1 | 7/2004 | MacPhee et al. |
| 7,320,962 | B2 | 1/2008 | Reich et al. |
| 7,666,803 | B2 | 2/2010 | Shetty et al. |
| 2002/0015724 | A1 | 2/2002 | Yang |
| 2005/0037051 | A1 | 2/2005 | Pendharkar |
| 2006/0088589 | A1 | 4/2006 | Gorman et al. |
| 2006/0257457 | A1 | 11/2006 | Gorman |
| 2009/0246238 | A1 | 10/2009 | Gorman et al. |
| 2010/0172958 | A1 | 7/2010 | Lucchesi |
| 2011/0045034 | A1 | 2/2011 | Nur |
| 2012/0177718 | A1 | 7/2012 | Asato et al. |
| 2013/0029030 | A1 | 1/2013 | Larsen |
| 2013/0066049 | A1 | 3/2013 | Van Dongen |

FOREIGN PATENT DOCUMENTS

| | | | |
|---|---|---|---|
| EP | 1462123 A1 | 9/2004 | |
| EP | 2596813 | 5/2013 | |
| JP | 57-153645 | 9/1982 | |
| JP | 06-142179 | 5/1994 | |
| JP | 11-507277 | 6/1999 | |
| JP | 2002-533164 | 10/2002 | |
| JP | 2004-521115 | 7/2004 | |
| JP | 2008-516736 | 5/2008 | |
| JP | 2013-522246 | 6/2013 | |
| WO | WO 1997/028832 A1 | 8/1997 | |
| WO | WO2005041811 A3 | 4/2006 | |
| WO | WO 2010/143711 | 12/2010 | |
| WO | WO2011083154 A1 | 7/2011 | |
| WO | WO 2011113436 A1 * | 9/2011 | ........... A61L 15/325 |
| WO | WO 2012/011429 | 1/2012 | |
| WO | WO 2013/004838 | 1/2013 | |
| WO | WO 2013/082073 | 6/2013 | |

OTHER PUBLICATIONS

International Preliminary Report on Patentability re: PCT/US2014/045000 dated Jan. 12, 2016.
International Search Report re: PCT/US2014/045000 dated Oct. 2, 2014.
Gelfoam Plus Hemostasis Kit (abbsorbable gelatin sponge, USP). Roberts, Ophthalmologic, Otolaryngologic, and Dental Procedures, Clinical Procedures in Emergency Medicine, 2010, p. 1216, 5th Edition.
Rubin, et al, Complete Dental Care of the Hemophiliac, Exodontia, 1959, pp. 665-675, n/a.

* cited by examiner

*Primary Examiner* — Dennis J Parad
(74) *Attorney, Agent, or Firm* — David Crichton; Leo Kriksunov (57) ABSTRACT

The present invention relates generally to agents and devices for promoting hemostasis and tissue sealing and, more particularly, to hemostatic pads comprising bioabsorbable scaffolds that can deliver lyophilized hemostasis promoting proteins, such as fibrinogen and thrombin, to a wound site or injured organ or tissue.

5 Claims, 8 Drawing Sheets

HEMOSTATIC PAD ASSEMBLY KIT AND METHOD

THE FIELD OF THE INVENTION

The present invention relates generally to agents and devices for promoting hemostasis and tissue sealing and, more particularly, to hemostatic pads comprising bioabsorbable scaffolds that can deliver lyophilized hemostasis promoting proteins, such as fibrinogen and thrombin, to a wound or injured organ or tissue.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical absorbable hemostats (TAHs) are widely used in surgical applications. TAHs encompass products based on various woven or non-woven fabrics or sponges, typically made of at least partially resorbable materials, ranging from natural to synthetic polymers and combinations thereof, including lactide-glycolide based co-polymers such as Polyglactin 910, oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and/or fibrinogen.

A number of hemostatic formulations are currently available on the market or in development that utilize lyophilized fibrinogen, frequently in combination with lyophilized thrombin, with hemostatic formulations that are applied in the form of dry powder, semi-liquid paste, liquid formulation, or optionally disposed on a supporting scaffold such as bioabsorbable fabric scaffold.

U.S. Pat. No. 7,320,962 entitled "Hemoactive compositions and methods for their manufacture and use", discloses a dried hemoactive material for inhibiting bleeding or delivering an agent, comprising: a cross-linked biologically compatible polymer which forms a hydrogel when exposed to blood; and a non-cross-linked biologically compatible polymer which solubilizes when exposed to blood: wherein the cross-linked polymer is dispersed in a dried matrix of the non-cross-linked polymer.

U.S. Pat. No. 6,706,690 entitled "Hemoactive compositions and methods for their manufacture and use", discloses a dried material which forms a hydrogel when exposed to blood, said material comprising: a cross-linked biologically compatible polymer which forms a hydrogel when exposed to blood; a non-cross-linked biologically compatible polymer which dissolves when exposed to blood; a plasticizer present in the non-cross-linked biologically compatible polymer; and wherein the cross-linked polymer is dispersed in a dried matrix of the non-cross-linked polymer, wherein the non-cross-linked biologically compatible polymer dissolves in 15 minutes or less when exposed to blood.

PCT Patent Publication No. WO 1997/028832 A1 entitled "Composition for Sealing Wounds" discloses a hemostatic bandage that contains powdered fibrinogen and thrombin adhered to a fibrous matrix with a viscous, nonaqueous adhesive such as a viscous polysaccharide, glycol, or petroleum jelly. The nonaqueous adhesive does not allow a hydrolytic reaction to occur between the fibrinogen and thrombin until the bandage is moistened by a body fluid, such as blood and teaches that the bandage can be prepared and stored for prolonged periods while retaining hemostatic activity. The reference further teaches a hemostatic wound dressing, comprising: a fibrous matrix suitable for placement as a pad applied over or inserted into an open, bleeding wound; a mixture of intermingled particles of powdered coagulation factors present on the surface of the matrix, the particles being in sufficiently close contact with each other to form a clot when exposed to an aqueous medium at a physiological pH, the particles being adhered to the matrix by a viscous nonaqueous adhesive, having a viscosity of at least 100 centipoise at 20° C., that inhibits a clotting reaction between the intermingled particles until the particles are exposed to an aqueous medium at physiological pH. The reference further discloses a hemostatic wound dressing, comprising: a fibrous matrix suitable for placement as a pad applied over or inserted into an open, bleeding wound; a mixture of intermingled particles of powdered coagulation factors present throughout the matrix, in sufficiently close contact to form a clot when exposed to an aqueous medium at a physiological pH, the particles being adhered to the matrix by a viscous nonaqueous adhesive that inhibits a clotting reaction between the intermingled particles until the particles are exposed to an aqueous medium at physiological pH, wherein the adhesive is selected from the group consisting of a polysaccharide, polyethylene glycol, propylene glycol, glycerol, and petroleum jelly, which adhesive has been applied to the matrix in a liquid form comprising less than 3% by weight water.

U.S. Patent Publication 2012/0177718 A1 entitled "Wound-Covering Material", by Chemo Sero Therapeutic Research Institute, discloses a wound-covering material that protects and repairs a wound area caused by an operation, trauma, burn, and the like. The description relates to a wound-covering material comprising thrombin, fibrinogen and a bioabsorbable supporting material. The wound-covering material may further be overlaid with a covering material for retaining moisture. The wound-covering material may consist of a kit of either (1) a bioabsorbable supporting material holding thrombin, and fibrinogen; or (2) a bioabsorbable supporting material holding thrombin, and a bioabsorbable supporting material holding fibrinogen; or (3) thrombin, fibrinogen and a bioabsorbable supporting material. Each of the kits may be combined with a covering material for retaining moisture.

U.S. Patent Publication US2013/0029030 A1 entitled "Method for Promotion of Hemostasis and/or Wound Healing", by Ferrosan Medical Devices A/S, discloses a matrix material comprising a pharmaceutical composition such as a matrix material with a pharmaceutical composition applied by ultrasonic spray technology on the surface. In one embodiment, the pharmaceutical composition comprises thrombin. The invention further describes a method for making the matrix material which has a pharmaceutical composition coated onto the surface of the matrix material using ultrasonic spray technology. In one specific embodiment, the invention also relates to the use of said matrix material for promotion of hemostasis and/or wound healing. The invention also relates to a kit-of-parts comprising a matrix with a pharmaceutical composition and a container with a peelable lid.

SUMMARY OF THE INVENTION

Briefly, in one embodiment, the present invention is directed towards a hemostatic wound treatment device having a bioabsorbable scaffold with a wound facing surface and an opposing surface. The scaffold is wetted with a biocompatible liquid that is not blood or plasma and a hemostatic powder adheres as a result of the moisture from the biocompatible liquid to at least the wound facing surface of said bioabsorbable scaffold. The hemostatic powder can be a mixture of dry fibrinogen and dry thrombin, dry fibrinogen, or dry thrombin. Dry, for purposes of this application means, that substantially all of the moisture has been removed from the material, preferably the residual water content is less than 4%, more preferably less than about 2% by weight. Hemostatic powder means, for purposes of this application, a material that is in its dry, particle form and biologically or physically active in some fashion in the hemostatic blood clotting cascade.

The biocompatible liquid can be selected from the group consisting of an aqueous solution, normal saline, ethanol, or ethanol-water mixture. In one embodiment, the biocompatible liquid can include a hemostatic agent. A hemostatic agent is a substance that is biologically or physically active in some fashion on the hemostatic blood clotting cascade. Exemplary hemostatic agents include thrombin, fibrinogen, hemostasis promoting agents, growth factors, calcium salts, absorbable disaggregation aids, bulking agents, gelatin, collagen, prothrombin, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, elastin, albumin, platelet surface glycoproteins, vasopressin, vasopressin analogs, epinephrine, selectin, procoagulant venom, plasminogen activator inhibitor, platelet activating agents, synthetic peptides having hemostatic activity.

In one embodiment, the scaffold has one or more layers constructed from materials of oxidized polysaccharide, bioabsorbable synthetic polymer or combinations thereof. In an alternative embodiment, the scaffold is a multi-layered structured composite material having a lactide-glycolide polymer layer and a cellulosic layer comprising oxidized regenerated cellulose that are attached to one another. The hemostatic powder is preferably provided on and adheres to the lactide-glycolide polymer layer, while the opposing surface layer comprises the oxidized regenerated cellulose that acts as a reinforcement and handling layer.

The present invention is also directed to a method of making and using the hemostatic wound treatment pad as described above by wetting the scaffold with the biocompatible liquid; contacting the scaffold with the hemostatic powder and adhering at least a portion of the hemostatic powder to at least the wound facing surface of the scaffold; and applying the wound facing surface of the hemostatic wound treatment pad onto a wound. The time period between initial contact of the scaffold with the hemostatic powder and the subsequent application of the hemostatic wound treatment pad onto the wound is preferably less than two minutes.

The present invention is also directed to a prep kit for a hemostatic wound treatment pad having at least one powdered hemostatic material; a bioabsorbable scaffold; a biocompatible liquid; and an application tray, wherein these components are combined into a unitary packaging unit. The at least one powdered hemostatic material can be a protein that is selected from the group consisting of fibrinogen, a thrombin, or a mixture thereof. The biocompatible liquid can be selected from the group consisting of water, an aqueous solution, a normal saline, a thrombin solution, a fibrinogen solution, an alcohol, or a glycerol. In one embodiment, the at least one powdered hemostatic material is a mixture of a dry fibrinogen and a dry thrombin and the biocompatible liquid comprises normal saline. In another embodiment, the powdered hemostatic material is dry fibrinogen and the biocompatible liquid is a thrombin containing solution. The kit can further include wetting means for wetting said bioabsorbable scaffold with the biocompatible liquid. Exemplary wetting means can be a liquid transfer pad; a spray bottle; a transfer pen; or a liquid tray having size accommodating immersion of said bioabsorbable scaffold with the wound facing side facing into said liquid tray. The liquid transfer pad includes a bundle of surgical gauze. The powdered hemostatic material can be packaged into the powder tray. The bioabsorbable scaffold can be constructed from one or more distinct layers of a bioabsorbable polysaccharide, a bioabsorbable synthetic polymer, a bioabsorbable protein, or combinations thereof. Alternatively, these materials of construction can be combined into unitary layers. The bioabsorbable scaffold can be a fabric, a woven material, a non-woven material, a mesh, or combinations thereof. In one embodiment, the bioabsorbable scaffold is a multilayer composite structure having a cellulosic layer comprising oxidized regenerated cellulose and a polymer layer comprising Polyglactin 910 that are separate, distinct and fixedly attached to one another.

DETAILED DESCRIPTION OF THE INVENTION

Briefly, the present invention is directed towards (i) a hemostatic pad in which biologics are moistly bound, preferably from a sterile, aqueous solution, more preferably a sterile saline solution, to at least one surface region by moisture, (ii) a kit for converting a bioabsorbable pad into a biologics containing-hemostatic pad in the operating room substantially prior to the use to stop bleeding and/or seal tissues on a patient in need, (iii) a method of assembling the hemostatic pad, and (iv) a method of treating the bleeding, providing hemostasis, and sealing the wound site or tissue with the hemostatic pad described above.

Figure 1:
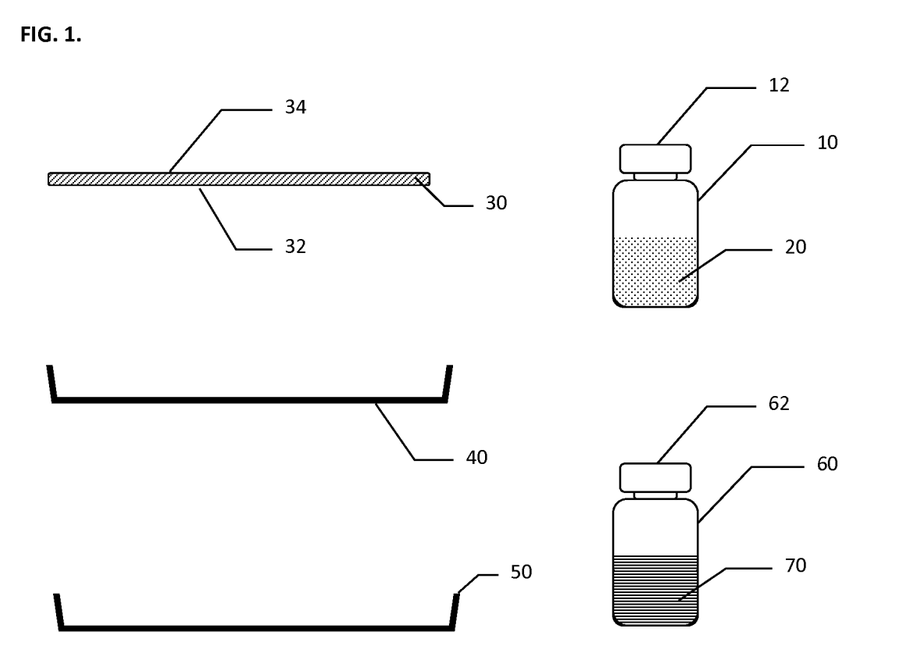
FIG. 1 schematically shows an embodiment of hemostatic pad assembly kit of the present invention.

Referring now to FIG. 1, an embodiment of the inventive hemostatic pad assembly kit is shown, with a hemostatic powder container 10 comprising a vial or a bottle hermetically sealed with a removable cap 12 and containing hemostatic powder 20. The hemostatic pad assembly kit further comprises supporting matrix, or scaffold 30, which is preferably biocompatible, bioabsorbable woven fabric or non-woven material or felt or combinations thereof. Scaffold 30 has wound facing side 32 and opposite top side 34 with wound facing side 32 and opposite top side 34 having optionally different properties such as being made of different materials. The hemostatic pad assembly kit further comprises a powder tray 40 and an optional liquid tray 50 and an optional liquid container 60 comprising a vial or a bottle hermetically sealed with a removable cap 62 and containing liquid 70.

Figure 2:
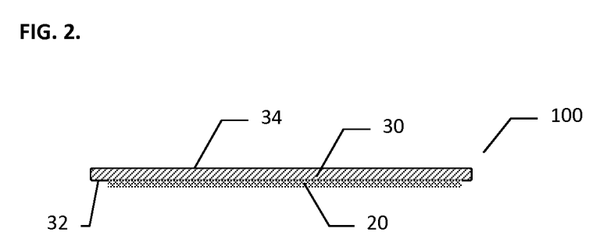
FIG. 2 schematically shows an embodiment of hemostatic pad of the present invention.

The hemostatic pad assembly kit shown in FIG. 1 and comprising hemostatic powder container 10, scaffold 30, powder tray 40, optional liquid tray 50, optional liquid container 60 is used to prepare a hemostatic pad 100 shown in FIG. 2, with hemostatic pad 100 comprising scaffold 30 coated on wound facing side 32 with hemostatic powder 20.

Figure 3:
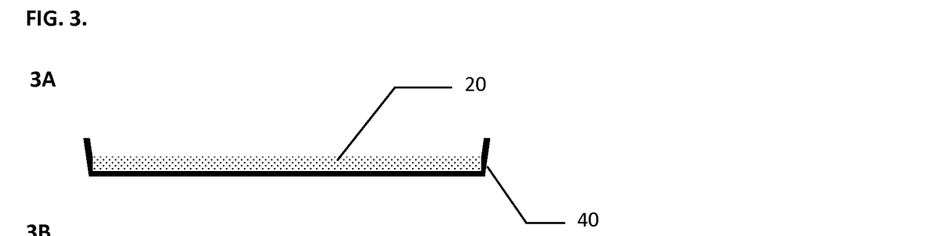
FIG. 3 schematically shows preparation of hemostatic pad of the present invention.

In certain embodiments, the preparation of hemostatic pad 100 from the inventive hemostatic pad assembly kit is performed as schematically illustrated in FIGS. 3-6. Referring now to FIG. 3, hemostatic powder 20 is transferred from hemostatic powder container 10 (not shown) into powder tray 40 (FIG. 3A); liquid 70 is transferred from liquid container 60 (not shown) into liquid tray 50 (FIG. 3B); scaffold 30 is immersed into liquid tray 50 with wound facing side 32 down, resulting in wetting of scaffold 30 with liquid 70 (FIG. 3C); scaffold 30 is immersed into powder tray 40 with wound facing side 32 down and brought into contact with hemostatic powder 20, resulting in adherence of at least a portion of hemostatic powder 20 to wound facing side 32 (FIG. 3D); resulting in forming of inventive hemostatic pad 100 comprising hemostatic powder 20 adherent to wound facing side 32 of scaffold 30 (FIG. 3E); immediately thereafter, the biologics-containing pad 100 is applied to a wound (not shown).

In certain embodiments, the amount of liquid 70 provided for wetting scaffold 30 is from about 2% of the volume of scaffold 30 to 90% or over 100% of the volume of scaffold 30. When volume of liquid 70 exceeds the amount of porosity of scaffold 30, excess of liquid 70 is not fully absorbed into scaffold 30. In a preferred embodiment, all liquid 70 is absorbed into scaffold 30, and volume of liquid 70 is from about 2% to about 70% of volume of scaffold 30, such as 5% or 25%. In a most preferred embodiment, all liquid 70 is absorbed into scaffold 30, with volume of provided liquid 70 being less than the volume of pores in scaffold 30, such as five (5) ml of liquid 70 is fully absorbed by scaffold 30 having volume of fifteen (15) cm$^3$ and porosity of about 50%, i.e. volume of pores in scaffold 30 is about 7.5 cm$^3$.

For an exemplary cuboid scaffold 30 having sides of 10 cm by 10 cm and a depth of 2 mm and consequently a volume of 20 cm$^3$, the volume of liquid 70 used for wetting scaffold 30 is 0.5 ml, 2 ml, 5 ml, or 10 ml. The shape of the scaffold is not limited to be a cuboid, meaning two sides with equal lengths and third side with a different dimension, but could be cube, meaning all sides of equal length, a right-angle parallelepided, meaning all sides of different lengths, or other substantially different geometric shapes suitable for use in surgical procedures.

Figure 4:
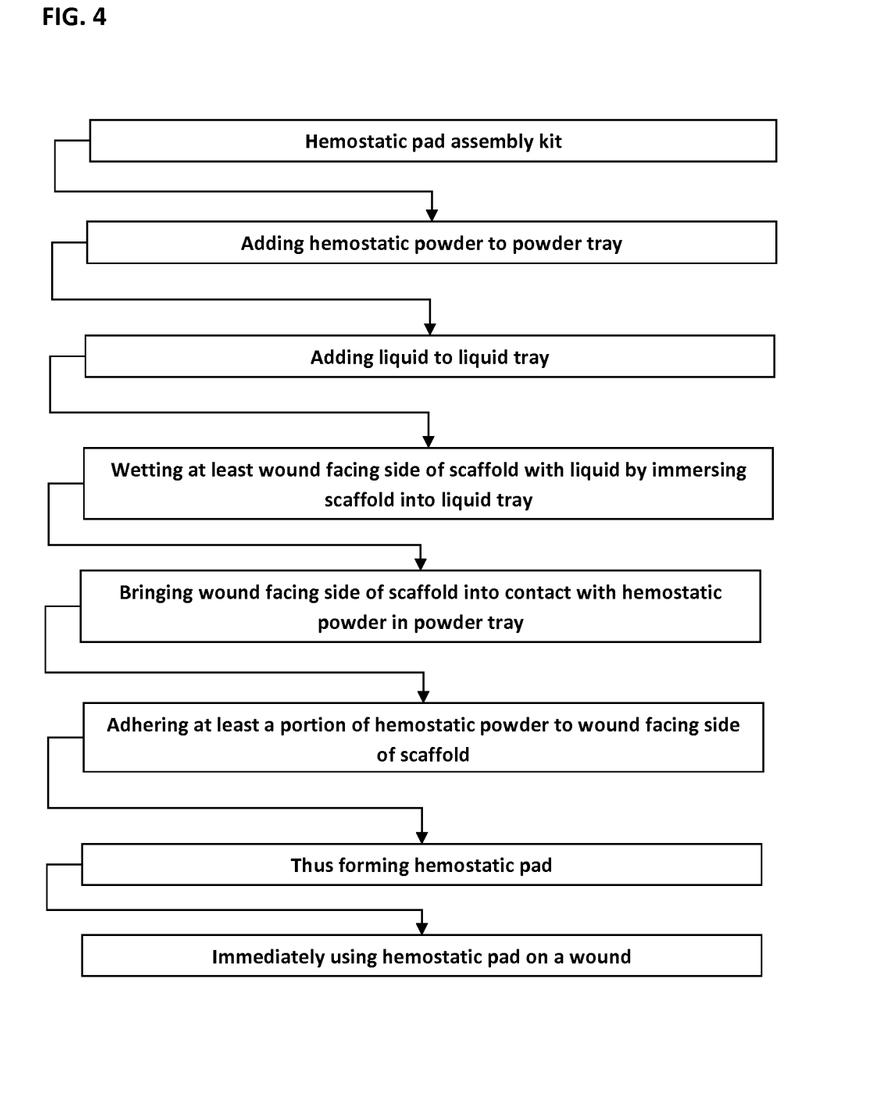
FIG. 4 schematically shows steps for assembly of hemostatic pad of the present invention.

Referring now to FIG. 4, in one embodiment, the sequence of steps for the method of preparation of the inventive hemostatic pad 100 is shown schematically. The preparation steps include: opening a hemostatic pad assembly kit; adding hemostatic powder to powder tray; adding liquid to liquid tray; wetting at least wound facing side of scaffold with liquid by immersing scaffold into liquid tray; bringing the wound facing side of scaffold into contact with hemostatic powder in powder tray; adhering by moisture at least a portion of hemostatic powder to wound facing side of scaffold to form the hemostatic pad and applying the hemostatic pad onto a wound, tissue or organ.

Figure 5:
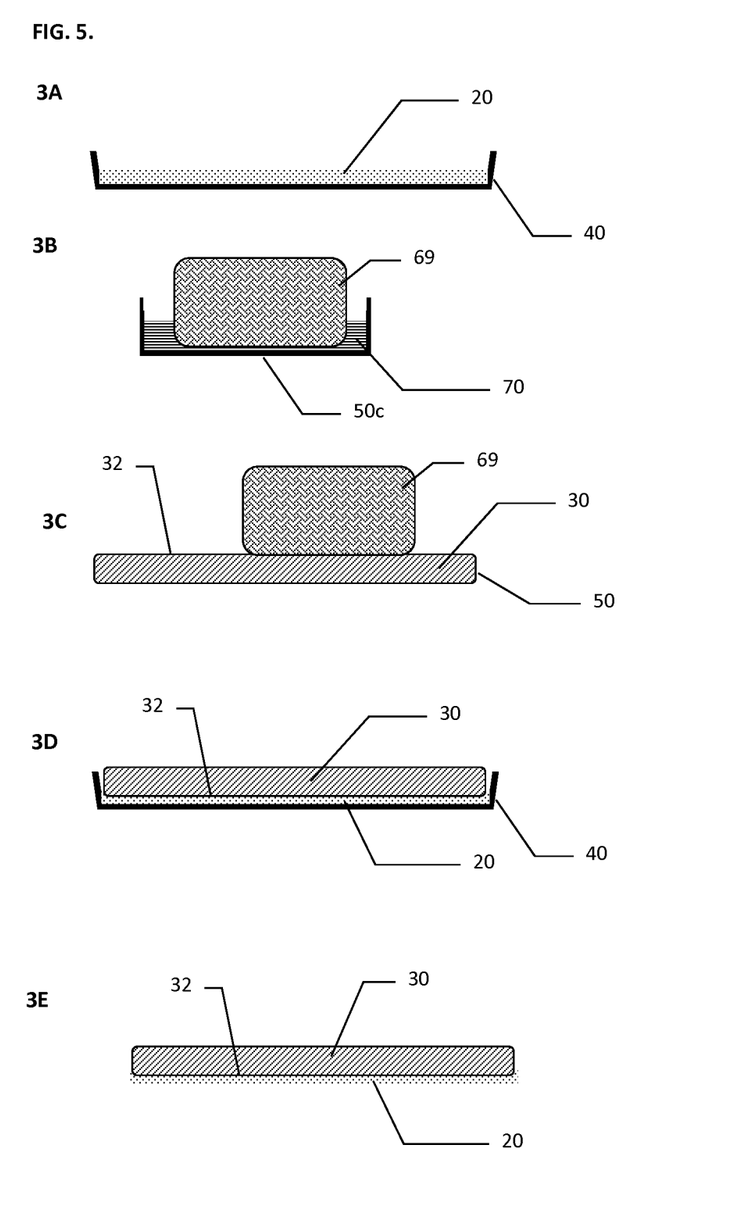
FIG. 5 schematically shows preparation of hemostatic pad of the present invention.

Referring now to FIG. 5, in a preferred embodiment, the preparation of hemostatic pad 100 from the inventive hemostatic pad assembly kit is performed with use of an intermediate liquid transfer pad, such as bundle of gauze 69. Bundle of gauze 69 is made of any sterile surgical gauze able to absorb at least 5-10% of water by volume and is utilized for transferring liquid 70. As illustrated in FIG. 5, to prepare hemostatic pad 100, hemostatic powder 20 is transferred from hemostatic powder container 10 (not shown) into powder tray 40 (FIG. 3A); bundle of gauze 69 is wetted with liquid 70 (optionally by transferring liquid 70 from liquid container 60 (not shown) into optional liquid tray 50c and immersing bundle of gauze 69 into optional liquid tray 50c (FIG. 3B); other ways of wetting bundle of gauze 69 such as by spraying are described below; scaffold 30 is then wetted on at least one wound facing side 32 by contacting with bundle of gauze 69 by gently dabbing scaffold 30 with bundle of gauze 69 (FIG. 3C); scaffold 30 is then immersed into powder tray 40 with wetted wound facing side 32 down towards powder 20 and brought into contact with hemostatic powder 20, resulting in adherence of at least a portion of hemostatic powder 20 to wound facing side 32 (FIG. 3D) to form the inventive hemostatic pad 100 comprising a hemostatic powder 20 that adheres by moisture to the wound facing side 32 of scaffold 30 (FIG. 3E); substantially soon (prior to significant conversion of fibrinogen to fibrin) after forming hemostatic pad 100, applying the moist biologics-containing hemostatic pad onto a wound, tissue or organ (not shown).

Figure 6:
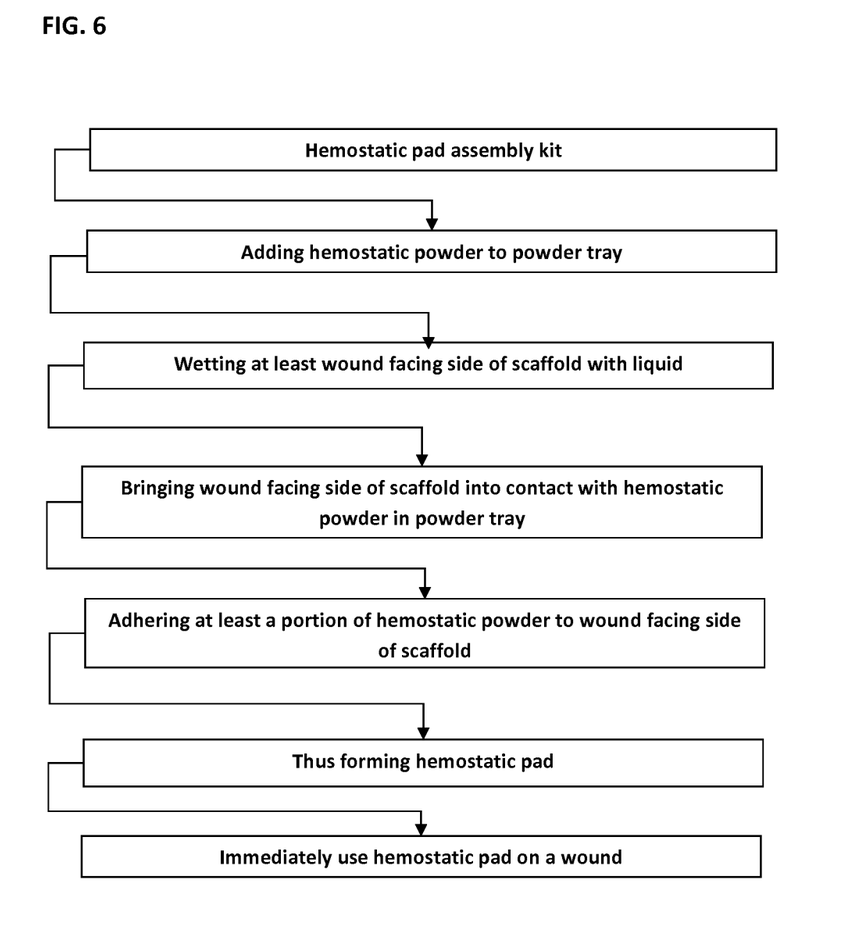
FIG. 6 schematically shows steps for assembly of hemostatic pad of the present invention.

Referring now to FIG. 6, in a preferred embodiment, the sequence of steps for the method of preparing inventive hemostatic pad 100 using a liquid transfer pad, such as bundle of gauze, without use of liquid tray or with optional use of liquid tray is shown schematically. The preparation steps include: opening a hemostatic pad assembly kit; adding hemostatic powder to a powder tray; wetting at least one wound facing side of scaffold with liquid using an intermediate liquid transfer pad, liquid spray, or other methods described below; bringing the wound facing side of scaffold into contact with hemostatic powder in powder tray to adhere at least a portion of hemostatic powder onto at least one wound facing side of scaffold to form hemostatic pad having hemostatic powder adhered by moisture thereto; and prior to substantial conversion of fibrinogen to fibrin, applying the hemostatic pad onto a wound, tissue or organ.

In the preferred embodiment shown in FIG. 6, the wetting step is performed with or without the use of liquid tray, by utilizing transfer pad, liquid spray, or other methods of wetting scaffold with liquid as known to these skilled in the art.

One method of wetting scaffold 30 with liquid 70 is by using an intermediate liquid transfer pad, such as surgical gauze. In this embodiment, surgical gauze is wetted with liquid 70 and then the wet gauze is utilized to transfer a portion of liquid 70 to scaffold 30 by gently dabbing scaffold 30 with wet gauze.

Immediately after assembly of the inventive biologics-containing hemostatic pad 100 and upon application to a bleeding site, the hemostatic powder proteins, when present as lyophilized fibrinogen and/or thrombin, are hydrated, reconstitute and initiate the conversion of fibrinogen to fibrin to form a fibrin clot upon the wound-facing portion of the hemostatic pad and the wound, tissue or organ in contact with the pad. Fibrin formation on the wound/tissue/organ surface promotes hemostasis and adhesion to the tissue. Thrombin and fibrinogen are capable of reacting and initiating conversion when placed in a moist state, even prior to application to the tissue. An extended period of time between assembly of hemostatic pad 100 and application to the wound, such as time in excess of several minutes, such as in excess of 5 minutes, could have a negative impact on performance in terms of hemostasis and adhesiveness to the wound. According to the instant invention, hemostatic pad 100 is applied to a wound substantially immediately after assembly, with time between the step of adhering at least a portion of hemostatic powder 20 to wound facing side 32 of scaffold 30 and application to the wound ranging from a few seconds, such as 2-3 seconds, to under 5 minutes, more preferably from about 5 seconds to about 2 minutes, most preferably from 10 seconds to 1 minute, such as 10 seconds, 30 seconds, or 60 seconds. The time between the first contact of scaffold 30 with hemostatic powder 20 and application to the wound is preferably under 5 minutes, most preferably about 2 minutes or less, such as 60 seconds, 90 seconds, or 120 seconds.

Figure 7:
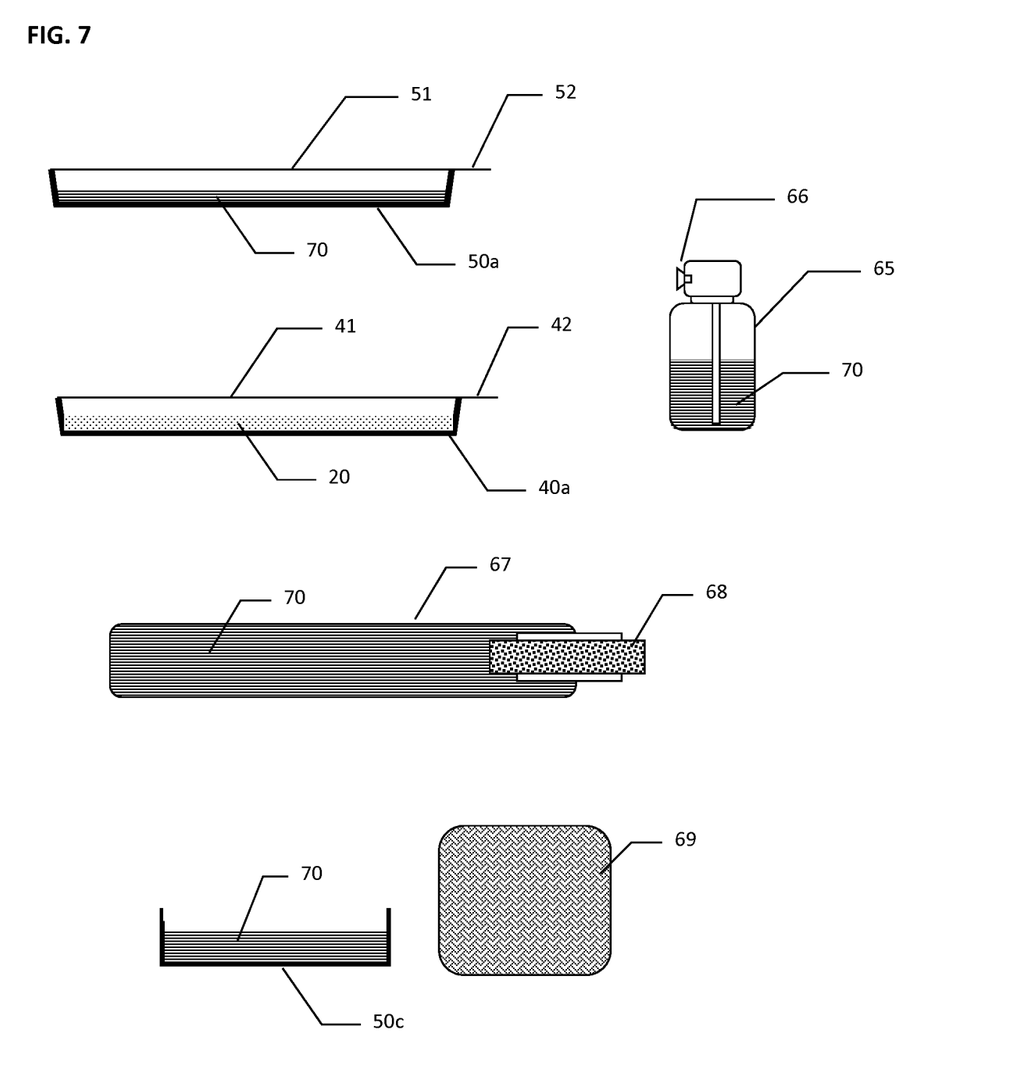
FIG. 7 schematically shows embodiments of components of hemostatic pad assembly kit of the present invention.

Referring now to FIG. 7, in some embodiments, hemostatic powder 20 is contained in powder tray 40a that is hermetically sealed with a removable, such as by peeling from an edge of powder tray 40a, lid 41 having optional lid tab 42 for ease of removal. In this embodiment, hemostatic pad assembly kit does not contain hemostatic powder container 10 and hemostatic powder 20 is stored directly in powder tray 40a.

In some embodiments, liquid 70 is contained in liquid tray 50a which is hermetically sealed with a removable, such as peelable lid 51 having optional lid tab 52 for ease of removal. In this embodiment, hemostatic pad assembly kit does not contain liquid container 60 and liquid 70 is stored directly in liquid tray 50a.

Referring to FIG. 7, in some embodiments liquid 70 is contained instead of liquid container 60 in a spray bottle 65 having spray mechanism 66. In this embodiment, the wetting step is performed optionally without use of liquid tray, by utilizing liquid spray for direct wetting of scaffold 30 with liquid 70. In yet another embodiment, liquid tray is utilized, with scaffold positioned in liquid tray with wound facing side 32 facing upwards, followed by spraying of liquid 70 onto wound facing side 32 from spray bottle 65. In some embodiments, spray mechanism 66 is a metered spray mechanism, delivering a metered amount of liquid with each spray.

Referring to FIG. 7, in some embodiments liquid 70 is contained in a pen-like dispenser 67 with a liquid transfer felt tip 68. In this embodiment, the wetting step is performed by transferring liquid 70 onto wound facing side 32 of scaffold 30 via the felt tip 68.

Referring to FIG. 7, in some embodiments liquid 70 is contained in liquid tray 50c and a bundle of gauze 69 made of any sterile surgical gauze able to absorb at least 10% of water by volume is utilized for transferring liquid 70. Bundle of gauze 69 is immersed into liquid tray 50c and then wet bundle of gauze 69 is brought into contact with wound facing side 32 of scaffold 30 to transfer liquid 70 to scaffold 30. Other means for transferring liquid 70 onto wound facing side 32 of scaffold 30 are contemplated and readily apparent to those skilled in the art upon review of this disclosure.

Figure 8:
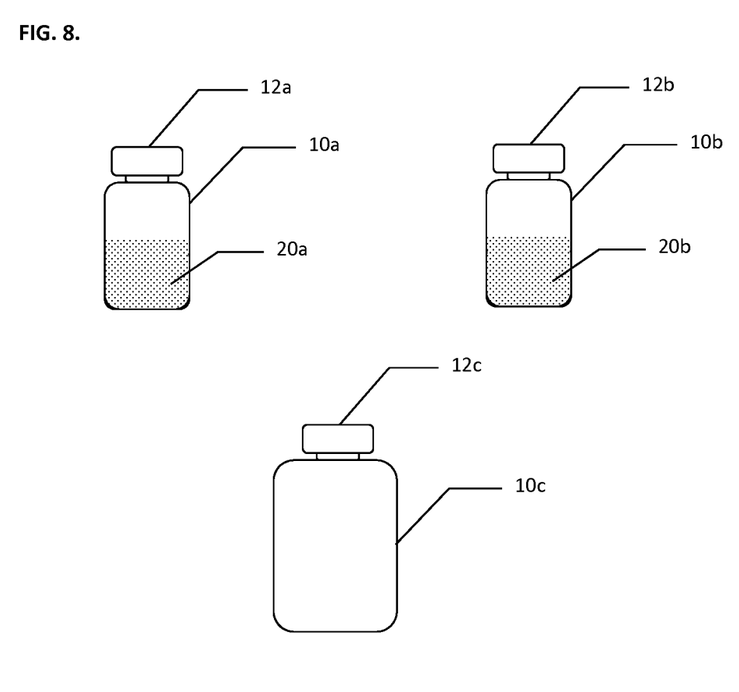
FIG. 8 schematically shows embodiments of components of hemostatic pad assembly kit of the present invention.

Referring now to FIG. 8, in some embodiments, there are provided two powder containers 10a and 10b for separate storage of the dry fibrinogen powder 20a and dry thrombin powder 20b, hermetically sealed with removable caps 12a and 12b, with the advantage of better shelf life due to separation of fibrinogen and thrombin, especially under difficult storage conditions of elevated temperature, humidity, and longer storage times. In use, dry fibrinogen powder 20a and dry thrombin powder 20b from their respective containers 10a and 10b are intermixed prior to contact with scaffold 30 that has been wetted with liquid 70. In one embodiment, the powders are mixed directly in powder tray 40. In one embodiment, the powders are mixed in one of the storage containers, such as container 10a or 10b. In yet another embodiment, there is provided an additional optional mixing container 10c, in which dry fibrinogen powder 20a and dry thrombin powder 20b are intermixed prior to use. Inert disaggregating bodies (not shown in FIG. 8) are optionally provided with the optional mixing container 10c and are described below.

Scaffold 30 is preferably made of at least partially resorbable, wound compatible, sterilizable material capable of absorbing at least some liquid 70. In some embodiments, scaffold 30 is made of bioabsorbable natural polymers, bioabsorbable synthetic polymers, or combinations thereof, including lactide-glycolide based co-polymers such as Polyglactin 910, oxidized cellulose (OC), oxidized regenerated cellulose (ORC), gelatin, collagen, chitin, chitosan, etc. Examples of natural or genetically engineered bioabsorbable polymers are proteins, polysaccharides and combinations thereof. Polysaccharides include, without limitation, cellulose, oxidized cellulose, oxidized regenerated cellulose (ORC), alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, starch, amylose, amylopectin, poly-N-glucosamine, polymannuronic acid, polyglucuronic acid, polyguluronic acid, and derivatives of any of the above.

Examples of synthetic bioabsorbable polymers are polyester polymers, copolymers, and/or combinations thereof. The polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one).

A preferred material for scaffold 30 of the present invention consists of a composite matrix of a knitted oxidized regenerated cellulose (ORC) backing layer under a layer of Polyglactin 910 (PG910) non-woven fibers. PG910 is a synthetic absorbable material composed of a copolymer made from 90% glycolide and 10% L-lactide. During the matrix manufacturing process, the PG910 fibers are carded into a batt and needle-punched to the ORC backing to produce scaffold 30. The PG910 side of the matrix is wound facing side 32 which will be coated with hemostatic powder 10.

A typical composition of scaffold 30 is about 5-30 mg/cm$^2$ of ORC (as a backing and reinforcing layer); and 5-30 mg/cm$^2$ of PG910 (as a biologics/hemostatic powder carrier layer), with the total matrix having weight of about 10-60 mg/cm$^2$. The teachings in U.S. Pat. No. 7,666,803 to Shetty, et al. entitled "Reinforced bioabsorbable multilayered fabric for use in medical devices" is incorporated herein by reference in its entirety for all purposes and teaches a multilayered fabric comprising a first bioabsorbable nonwoven fabric and a second bioabsorbable woven or knitted fabric comprising oxidized polysaccharides. The teachings in published U.S. Patent Application 2009/0246238 A1 by Gorman et al., entitled "Reinforced Bioabsorbable Multilayered Hemostatic Wound Dressing" is incorporated herein by reference in its entirety for all purposes and teaches a method for making a multi-layered wound dressing having a first bioabsorbable nonwoven fabric, one or more second bioabsorbable woven or knitted fabric, thrombin and/or fibrinogen, comprising the steps of: (a) crimping bioabsorbable polymer fibers or yarns in the range of about 10 to 30 crimps per inch; (b) cutting the crimped fibers or yarns to a staple length between about 0.1 and 2.5 inch; (c) carding the staple to form the first bioabsorbable nonwoven fabric while controlling the humidity to about 20 to 60%, at a room temperature of about 15 to 24° C.; (d) attaching the first bioabsorbable nonwoven fabric to the second bioabsorbable woven or knitted fabric. The reference further discloses a method for making a wound dressing comprising bioabsorbable nonwoven fabric, thrombin and/or fibrinogen, comprising the steps of: (a) suspending the thrombin and/or fibrinogen in a perfluorinated hydrocarbon to form a suspension; and (b) applying the suspension to the bioabsorbable nonwoven fabric.

The teachings in published U.S. Patent Application 2006/0088589 A1, entitled "Method for making an absorbable hemostat", Gorman et al., is also incorporated herein by reference in its entirety for all purposes, and discloses a method of making a wound dressing, characterized in that said method comprises: suspending thrombin and/or fibrinogen powder in a perfluorinated hydrocarbon carrier fluid in which they are not soluble, and applying the resulting suspension to a first absorbable nonwoven fabric.

In one embodiment, scaffold 30 is a uniform material, with wound facing side 32 and opposite top side 34 having the same properties. In some embodiments, scaffold 30 is made of woven or non-woven ORC fabric or felt. In other embodiments, scaffold 30 is made of PG910 woven or non-woven fabric or felt.

In some embodiments, a non-woven ORC-based material, such as the material commercially available from Ethicon as SURGICEL® SNoW™ absorbable hemostat, can be used as scaffold 30. In other embodiments, woven ORC-based materials, such as the materials commercially available from Ethicon as SURGICEL® Original absorbable hemostat and SURGICEL® NU-KNIT® absorbable hemostat; and non-woven ORC-based material, such as the materials commercially available from Ethicon as SURGICEL® FIBRILLAR™ absorbable hemostat, can be used as scaffold 30.

Scaffold 30 preferably is sized and having dimensions that are selected so as to fully or at least partially cover the wound of treatment site. In some embodiments, scaffold 30 is a flat article having from a top or bottom perspective, a triangular, rectangular, elliptical, polygonal or any other geometric shape. The thickness of scaffold 30 is from about 0.2 mm to about 5 mm, preferably from about 0.5 mm to about 3 mm, such as 1 mm. The dimensions of a wound-facing or opposing surfaces are preferably square shaped, from about 2 cm by 2 cm or less to about 20 cm by 20 cm or larger, such as 10 cm by 10 cm.

Various hemostatic materials in the form of dry powders are contemplated for use herein. In the preferred embodiment, hemostatic powder 20 comprises a mixture of dry (such as lyophilized or spray dried) fibrinogen and dry (such as lyophilized or spray dried) thrombin, with optional additional components, excipients, and stabilizers. Additives can further include hemostasis promoting agents, growth factors, calcium salts, absorbable disaggregation aids, bulking agents, gelatin, collagen, and combinations thereof. Hemostasis promoting agents include proteins, prothrombin, thrombin, fibrinogen, fibrin, fibronectin, heparinase, Factor X/Xa, Factor VIINIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof.

In one embodiment, the composition of hemostatic powder 20 in the overall kit is from about 50% to about 95% fibrinogen by weight, with balance being thrombin and optional excipients and stabilizers. The particle size of hemostatic powder 20 is from about 5-20 microns to about 3-5 mm, more preferably from about 50 microns to about 2 mm.

In some embodiments, the amount of hemostatic powder 20 in the overall kit is sufficient for the preparation of one hemostatic pad 100, and in other embodiments, the amount sufficient for preparation of several hemostatic pads 100, such as 2, 3, 5, or 10 hemostatic pads 100. The weight of hemostatic powder 20 for preparation of one hemostatic pad 100 ranges from about 10 mg to about 5 g, such as 50 mg, 500 mg, 2000 mg, when using the hemostatic powder which is principally dry fibrinogen and/or dry thrombin.

The quantities of fibrinogen and thrombin (as dry powders) when applied together onto a wound-facing surface of the hemostatic biologics-containing pad 100 is preferably from about 1-200 mg/cm$^2$ fibrinogen, more preferably 2-20 mg/cm$^2$ fibrinogen, such as 10 mg/cm$^2$ fibrinogen and 1-500 IU/cm$^2$ thrombin, more preferably 1-150 IU/cm$^2$ thrombin, such as 50 IU/cm$^2$ thrombin; with other excipients present, such as calcium chloride, optional arginine, glycine, albumin, mannitol, buffer salts and other optional protein components conventionally found in dried blood plasma derived products.

The biological components of the hemostatic biologics-containing pad are preferably the lyophilized or spray dried forms of the human or animal source fibrinogen and human or animal source thrombin substances. The fibrinogen and thrombin substances can alternatively be obtained recombinantly or derived synthetically in known fashion.

In a preferred embodiment, liquid 70 comprises sterile normal saline solution. In other embodiments, liquid 70 comprises, purified water, such as water for injection, or aqueous solution of excipients or materials that may enhance hemostasis, clot stability, strength and/or otherwise inhibit clot lysis. One exemplary additive is calcium, a sterilized Ca-salt containing solution embodiment.

In one embodiment, liquid 70 comprises a non-aqueous solvent, such as ethanol, or ethanol/water mixture. Advantageously, ethanol or ethanol/water mixture is expected to slow down the reconstitution of hemostatic powders and resulting formation of fibrin during preparation of hemostatic pad 100.

In one embodiment, liquid 70 contains dissolved thrombin or another fibrinogen activator, while powder container 10 contains primarily fibrinogen. In use, scaffold 30 is wetted with liquid 70 containing thrombin and then scaffold 30 is contacted with fibrinogen-based hemostatic powder. Advantageously, due to separation of fibrinogen and thrombin, such a kit should exhibit better shelf life, especially under difficult storage conditions of elevated temperature, humidity, and longer storage times would be expected.

Powder container 10 and removable cap 12 are made of a material providing sufficient barrier for the long term storage of hemostatic powder 20, i.e. very low gas and moisture permeability, with preferred materials are known including polymers, coated polymers, and glass which are known to a skilled artisan. The size of the powder container 10 is selected so as to accommodate hemostatic powder 20 with optional unfilled space being from about 10% to about 90% of powder container 10.

In some embodiments, powder container 10 can accommodate the amount of hemostatic powder 20 sufficient for preparation of one hemostatic pad 100, and in other embodiments, powder container 10 can accommodate the amount of hemostatic powder 20 sufficient for preparation of several hemostatic pads 100, such as 2, 3, 5, or 10 hemostatic pads 100. The volume of powder container 10 can range from about 1 ml to about 50 ml, such as 5 ml, 10 ml, or 20 ml.

Figure 9:
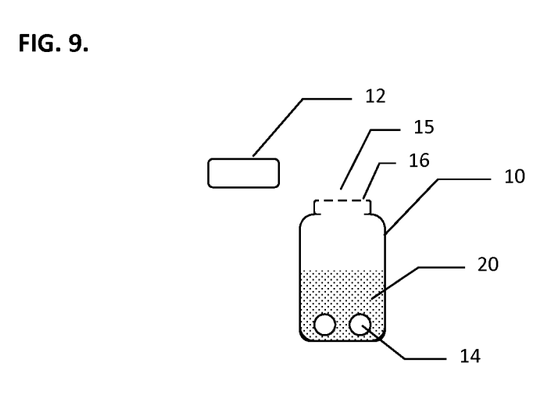
FIG. 9 schematically shows embodiments of components of hemostatic pad assembly kit of the present invention.

As shown in FIG. 9, in one embodiment, powder container 10 can also optionally contain inert disaggregating bodies, such as at least one disaggregating ball 14, which can be made of any inert material, such as metal, plastic, glass, and the like. Powder container 10 can also optionally have a sieve-like mesh 15 with apertures 16 covering container 10 exit, with apertures 16 being sized so as to permit pouring of hemostatic powder 20, but not to permit exit from powder container 10 of optional disaggregating balls 14 or large agglomerates of hemostatic powder 20. In use, prior to the transfer of hemostatic powder 20 from powder container 10, powder container 10 with or without disaggregating balls 14, is vigorously shaken with removable cap 12 still on powder container 10 for a period of time sufficient for substantially disaggregating hemostatic powder 20. Time for disaggregating hemostatic powder is from about 3 seconds to about 60 seconds, such as 10 seconds.

Liquid container 60 and removable cap 62 are made of a material providing sufficient barrier for the long term storage of liquid 70, i.e. very low gas and moisture permeability, with preferred materials including polymers, coated polymers, and glass which are known to a skilled artisan. The size of liquid container 60 is selected so as to accommodate liquid 70 with optional unfilled space being from about 10% to about 90% of liquid container 60.

In some embodiments, liquid container 60 can accommodate the amount of liquid 70 sufficient for preparation of one hemostatic pad 100, and in other embodiments, liquid container 60 can accommodate the amount of liquid 70 that is sufficient for preparation of several hemostatic pads 100, such as 2, 3, 5, or 10 hemostatic pads 100. The volume of liquid container 60 can range from about 0.5 ml to about 50 ml, such as 2 ml, 5 ml, 10 ml, or 20 ml.

Dimensions of powder tray 40 and liquid tray 50 are selected so as to fully accommodate scaffold 30 in a flattened position in each tray. The contemplated dimensions are as follows: geometrical shape of each tray is identical to geometrical shape of scaffold 30, but dimensioned larger than dimensions of scaffold 30 by 0% to 10%, such as 1% or 3%. The depth of each tray is dimensioned to be from about one half of the thickness of scaffold 30 to about 10 times greater than the thickness of scaffold 30. In some embodiments, the depth of trays is 2 mm, 5 mm, or 10 mm.

In one embodiment, the present invention is directed to a hemostatic or tissue sealing material or pad on which a hemostatic powder moistly adheres to at least one surface thereof. In another embodiment, the present invention also relates to a method of preparing or assembling the hemostatic or tissue sealing material or pad. In another embodiment, the present invention also relates to a method of providing a hemostatic treatment or tissue sealing to a wound site, comprising the steps of: (a) forming the hemostatic or tissue sealing material or pad as described above, and (b) applying the hemostatic or tissue sealing material to the wound site.

The inventors have surprisingly and unexpectedly discovered, that preparing pre-activated fibrinogen/thrombin mixture based hemostatic pad 100 as described above resulted in excellent adherence of hemostatic powder 20 to scaffold 30 and in excellent adherence of thus prepared hemostatic pad 100 to wound tissue, as well as rapid hemostatic action. No significant loss of hemostatic and adhesive properties was observed. The inventors have further surprisingly discovered that capillary forces developed between wetted surface of scaffold 30 and dry powder particles were sufficiently strong to hold dry hemostatic powders on wound facing side of scaffold 30 for a sufficient time for transfer of hemostatic pad 100 to a wound site.

While the following examples demonstrate certain embodiments of the invention, they are not to be interpreted as limiting the scope of the invention, but rather as contributing to a complete description of the invention.

Example 1. Hemostatic Test of Inventive Hemostatic Pad Preparation and Use

A scaffold made of composite matrix of a knitted oxidized regenerated cellulose (ORC) backing layer under a layer of Polyglactin 910 (PG910) non-woven fibers as described above was utilized. A dry hemostatic powder (lyophilized) derived from animal origin (porcine) was utilized. Approximately three hundred ninety (390) mg of thrombin powder (having about 20 IU/mg active thrombin) and about seventeen hundred (1700) mg of fibrinogen powder (containing about 0.4 mg/mg clottable fibrinogen) were available. The hemostatic powders were disaggregated from aggregated cake that formed during storage. The thrombin and fibrinogen powders were then transferred into a powder tray and thoroughly mixed and evenly distributed in the tray. The scaffold in this test was cut to size to cover end of kidney with approximately a one (1) cm margin, size of the scaffold was 3.5 cm×2.5 cm rectangular pieces.

A surgical practitioner performed a partial nephrectomy by surgically removing approximately three (3) cm of distal kidney with holding and maintenance of pressure on kidney to temporary halt bleeding. The scaffold was positioned in a sterilized tray, and surgical gauze was wetted with saline and then dabbed on the scaffold insuring that all of PG910-based scaffold surface was moist. The scaffold was then placed into tray containing lyophilized hemostatic powders of fibrinogen and thrombin with wet surface down, and briefly tapped down to insure satisfactory hemostatic powder pick up and adherence. The moistened scaffold was observed to effectively pick up and hold the lyophilized hemostatic powders.

Scaffold with the hemostatic powders adhering to one side of the scaffold was then immediately transferred to the target bleeding site. The transfer and placement was accomplished in less than sixty (60) seconds. Pressure was applied on the scaffold that had been positioned on the wound for three (3) minutes.

The inventors observed that the hemostatic powder was picked up and reliably adhered to the wet scaffold. The three (3) minute pressure period was sufficient to completely stop bleeding. Control of hemorrhage and adherence to the underlying tissue was similar to known hemostatic pads on which had dry hemostatic powders were pre-attached to scaffolds. Surprisingly, transfer to bleeding site could be accomplished without prematurely activation of the hemostatic powders to a degree that materially diminished effectiveness of hemostasis and tissue adherence.

In the ascending artery bleeding model, the ascending aortic artery of the pig was exposed using a scalpel for five (5) mm longitudinal incision in the abdominal aorta in a porcine model. Tamponade was applied to temporarily stop the bleeding. After the excess blood was aspirated off, a hemostatic powder-loaded hemostatic pad prepared as described above was applied to the wound site, followed by a piece of wet gauze, and manual compression. After three (3) minutes, bleeding stopped, proving the effectiveness of the hemostatic pad as a hemostat. The adhesion of the hemostatic pad to the tissue was assessed by pulling the sample with a pickup. Relatively high force was required to separate the sample from the tissue.

Example 2. Demonstration of Scaffold Wetting and Adherence

Exemplary scaffold materials that were used are as follows:
Specimen SF: lightweight, layered ORC based absorbable hemostatic material;
Specimen SS—structured non-woven fabric, needle punched with interlocking fibers, ORC based absorbable hemostatic material;
Specimen SO—loose knit ORC based absorbable hemostatic material;
Specimen CM or composite matrix, whereby the scaffold was made of composite multi-layer matrix of a knitted oxidized regenerated cellulose (ORC) reinforcing backing layer under a layer of Polyglactin 910 (PG910) non-woven fibers as a hemostatic powders carrier layer. Lyophilized biologic materials that were used as the hemostatic powders tested were: Bioseal Fibrinogen (~850 mg per 5-ml vial); Bioseal Thrombin; (~78 mg per 5 ml vial).

Soaking Method. One vial each of fibrinogen and thrombin was milled into powder in the respective vials, followed by combining both hemostatic powders and mixing them in one vial by hand shaking. The mixed hemostatic powder then was transferred into a five (5) by ten (10) cm plastic tray, larger hemostatic powder particles and agglomerates were crushed with a pestle, and the blended, disagglomerated hemostatic powder was then evenly distributed in the tray. Five (5) ml of normal saline was transferred into another five (5) by ten (10) cm tray. A scaffold was cut to size of five (5) cm by ten (10) cm, then placed into the tray containing saline in a flat orientation and allowed to soak for about fifteen (15) seconds. The wet scaffold was then transferred into the tray containing the blended, disagglomerated hemostatic powder and placed into the hemostatic powder in a flat orientation, with light tapping on the top exposed surface of the scaffold throughout the area for about 30 seconds to allow and enhance hemostatic powder pickup. The hemostatic powder loaded scaffold was then removed from the tray and the remaining hemostatic powder in the powder tray was observed to analyze the completeness of the pickup of the hemostatic powder by the scaffold.

The results of the pick-up test demonstrated that Specimen SF absorbed the solvent quickly and completely, the top layers of the scaffold were still dry; Specimen SF picked up the most of the hemostatic powder in the soaking method; Specimen SS did not pick up all of the liquid from the tray and picked up the least of hemostatic powder relative to the other test substrates. Specimen SO deformed after soaking and there was still liquid left. While it picked some hemostatic powder, it was not used in further testing. Specimen CM, the composite matrix absorbed some liquid but there was some left in the tray. The composite matrix did not pick-up any hemostatic powder; instead, the hemostatic powder was wetted and reacted in the powder tray. Overall, it was observed that the use of an excess of liquid, i.e. up to fully soaking composite matrix or other specimens in liquid, did not improve the degree of hemostatic powder pick-up and adherence.

Wiping method for Wetting. The experimental setup and materials were similar to the conditions and materials described above. Instead of wetting the scaffold in a tray with liquid, a surgical gauze was used as a liquid transferring means, whereby the gauze was dipped into container containing ten (10) ml of normal saline, wetted, then lightly and quickly applied to the two and half (2.5) cm by ten (10) cm scaffold surface Immediately thereafter, the scaffold was transferred into the blended, disagglomerated hemostatic powder tray in a flat orientation with the wetted surface down and in contact with the hemostatic powder, with light tapping on the top exposed surface of the scaffold throughout the area for about 30 seconds, allowing hemostatic powder pickup. The hemostatic powder loaded scaffold was then removed from the tray and the remaining hemostatic powder in the powder tray was observed to analyze the completeness of the pickup of the hemostatic powder by the scaffold. The results of the test demonstrated that Specimen SS and Specimen CM, Composite Matrix scaffold picked-up most hemostatic powder.

Example 3. Tissue Adhesion Evaluation

The composite matrix (Specimen CM) and Specimen SS, as described above, were further tested for tissue adhesion. The selected scaffolds were pre-cut into three quarter (¾) by four (4) inch strips and then coated with the blended, disagglomerated hemostatic powders directly before placing the sample strips onto the bovine corium to test for adhesion strength by evaluation of three different groups (number of tests in each group N=4) of hemostatic powder mixtures that each contain a different combination of hemostatic powders and scaffolds. The hemostatic powder dosages were prepared at the testing site and include the following: Specimen SS (Non-woven ORC) coated with blended disagglomerated hemostatic powders containing Fibrinogen: total of 130 mg or 6.7 mg/cm$^2$; Thrombin: total of 1450 IU or 75 IU/cm$^2$; Calcium Chloride total of 18 mg or 0.93 mg/cm$^2$. Specimen CM (Composite Matrix) coated with blended disagglomerated hemostatic powders containing Fibrinogen: total of 130 mg or 6.7 mg/cm$^2$; Thrombin: total of 1450 IU or 75 IU/cm$^2$; Calcium Chloride total of 18 mg or 0.93 mg/cm$^2$. Specimen CM (Composite Matrix) coated with disagglomerated hemostatic powders containing Fibrinogen: total of 130 mg or 6.7 mg/cm$^2$; Thrombin: total of 484 IU or 25 IU/cm$^2$; Calcium Chloride total of 18 mg or 0.93 mg/cm$^2$.

The following procedure summarizes the steps to prepare the samples for peel adhesion strength testing: Mill the Bioseal thrombin and fibrinogen into powder form within the original vials using a spatula. Mix three 5-ml vials of Bioseal Thrombin into one 5-ml vial of Bioseal Fibrinogen to obtain the 6.7 mg/cm$^2$ fibrinogen and 75 IU/cm$^2$ thrombin mixture for test groups that require 75 IU/cm2 of Bioseal thrombin. Shake the mixture in the one vial by hand until the hemostatic powders are well mixed. Mix one 5-ml vial of Bioseal Thrombin with one 5-ml vial of Bioseal Fibrinogen to obtain the 6.7 mg/cm2 fibrinogen and 25 IU/cm2 thrombin mixture. Shake the mixture in the vial by hand until the hemostatic powders are well mixed. Dispense the hemostatic powder mixtures and evenly distribute the hemostatic powder a into 5 cm×10 cm plastic tray. Place 1-2 ml of saline into a small container and wet gauze with saline. Transfer saline from the wetted gauze onto the pre-cut ¾×4 inch strips of scaffold lightly and quickly to cover the entire area of the strip. Position the wetted scaffold in a flat orientation into the powder tray with wetted surface down towards the hemostatic powder and lightly press the scaffold into the hemostatic powder. Remove thus prepared fibrin pad and transfer it for immediate testing of peel force (adhesion strength) on corium.

Tests of adhesion strength (peel force) were performed at ambient conditions according to a standard testing protocol as described below. The equipment, including Model 5544 Instron TJ-041; Instron 10-N load cell (LC-145); Digital Balance: SE-109; Bovine Calf Corium (Lampire Biologicals). The test method for use in determining the tissue adhesion strength on a calf corium tissue substrate was as follows. The test directly measures the average force necessary to perform a 90 degree peel of a hemostatic pad product from calf corium tissue. Briefly, the hemostatic pad is applied to the surface of the corium tissue and a dead weight is applied to the product to simulate tamponade. The peel strength force is the measured as an indication of tissue adhesion properties of the hemostatic pad.

Prepared corium samples with a thickness of at least 0.040" were soaked in 0.1% KOH solution and then rinsed with water; the samples were then soaked in saline solution. A piece of corium was then secured on a support and brought to 37+−1° C. 3 ml of TBS was evenly sprayed onto the corium surface and excess moisture was then removed from the surface. The hemostatic pad was then placed onto the corium tissue, biologics-containing side down and the tamponade weight positioned on top, allowing the incubation to proceed for 3 minutes. The tamponade weight was then removed and the hemostatic pad connected via a clamp to the Instron tension rod, after which the pull test started. The results are then presented as calculated peel force (N)/ hemostatic pad Strip Width (m)=N/m.

The results of the peel force testing are presented in Table 1.

TABLE 1

| | CM [Composite Matrix] 6.7 mg/cm$^2$ fibrinogen and 75 IU/cm$^2$ thrombin (1:3 ratio of fibrinogen:thrombin) | Peel Force/ Width (N/m) | | CM [Composite Matrix] 6.7 mg/cm$^2$ fibrinogen and 25 IU/cm$^2$ thrombin (1:1 ratio of fibrinogen:thrombin) | Peel Force/ Width (N/m) | | Specimen SS 6.7 mg/cm$^2$ fibrinogen and 75 IU/cm$^2$ thrombin (1:3 ratio of fibrinogen:thrombin) | Peel Force/ Width (N/m) |
|---|---|---|---|---|---|---|---|---|
| | Test #1 | 54.63 | | Test #1 | 149.33 | | Test #1 | 33.22 |
| | Test #2 | 40.53 | | Test #2 | 84.77 | | Test #2 | 24.35 |
| | Test #3 | 106.08 | | Test #3 | 93.20 | | Test #3 | * |
| | | | | | | | *test failed due to failure of scaffold strength | |
| | Test #4 | 75.02 | | Test #4 | 85.37 | | | |
| | Mean | 69.2 (N = 4) | | Mean | 103.2 (N = 4) | | Mean | 28.8 (N = 2) |

Analysis of the data in Table 1 indicates that Composite Matrix scaffolds with 6.7 mg/cm$^2$ fibrinogen and 25 IU/cm2 Bioseal thrombin (1:1 ratio of thrombin:fibrinogen) or the 6.7 mg/cm$^2$ fibrinogen and 75 IU/cm2 Bioseal thrombin (3:1 ratio of thrombin:fibrinogen) had greater peel adhesion strength compared to the Specimen SS scaffolds. The coatings with 6.7 mg/cm$^2$ fibrinogen and 25 IU/cm$^2$ thrombin (1:1 ratio of fibrinogen: thrombin) produced somewhat higher mean peel strength vs. the coatings with 6.7 mg/cm$^2$ fibrinogen and 75 IU/cm$^2$ thrombin (1:3 ratio of fibrinogen: thrombin); however some individual readings were comparable in these two groups. From the data presented, it is evident that preparation of the inventive hemostatic device using methods of the instant invention resulted in high adhesion strength that was comparable to a fibrin pad that had been manufactured and stored with dry hemostatic powders pre-coated on the wound-facing surface.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

We claim:

1. A method of making and using a hemostatic wound treatment device comprising: a bioabsorbable scaffold having a wound facing surface and an opposing surface; and a hemostatic powder that comprises a mixture of fibrinogen and thrombin, the method comprising:
   a) wetting the scaffold with the biocompatible liquid that is not blood or plasma selected from the group consisting of an aqueous solution, normal saline, ethanol, and ethanol-water mixture; then
   b) contacting the scaffold with the hemostatic powder in dry form in a powder tray onto the wet scaffold and adhering at least a portion of the hemostatic powder to at least the wound facing surface of the scaffold; and then c) applying the wound facing surface of the hemostatic wound treatment pad onto a wound.

2. The method of claim 1 wherein the scaffold comprises an oxidized polysaccharide or bioabsorbable synthetic polymer.

3. The method of claim 1 wherein the scaffold is a multi-layered structured composite material comprising a lactide-glycolide polymer layer and a cellulosic layer comprising oxidized regenerated cellulose.

4. The method of claim 1 wherein the hemostatic powder adheres to the lactide-glycolide polymer layer and the opposing surface layer comprises the oxidized regenerated cellulose.

5. The method of claim 1 wherein the time period between initial contact of the scaffold with the hemostatic powder and the subsequent application of the hemostatic wound treatment pad onto the wound is less than two minutes.

* * * * *